United States Patent
Fritz et al.

(10) Patent No.: US 10,161,859 B2
(45) Date of Patent: Dec. 25, 2018

(54) PLANAR REFLECTIVE RING

(71) Applicant: Honeywell International Inc., Morris Plains, NJ (US)

(72) Inventors: Bernard Fritz, Eagan, MN (US); Teresa Marta, White Bear Lake, MN (US); Chad Langness, Morris Plains, NJ (US)

(73) Assignee: Honeywell International Inc., Morris Plains, NJ (US)

( * ) Notice: Subject to any disclaimer, the term of this patent is extended or adjusted under 35 U.S.C. 154(b) by 117 days.

(21) Appl. No.: 15/336,364

(22) Filed: Oct. 27, 2016

(65) Prior Publication Data

US 2018/0120222 A1    May 3, 2018

(51) Int. Cl.
| | |
|---|---|
| *G01N 21/35* | (2014.01) |
| *G01N 21/3504* | (2014.01) |
| *G01J 1/04* | (2006.01) |
| *G01J 1/16* | (2006.01) |
| *G01N 21/03* | (2006.01) |

(52) U.S. Cl.
CPC ........ *G01N 21/3504* (2013.01); *G01J 1/0422* (2013.01); *G01J 1/1626* (2013.01); *G01N 21/031* (2013.01)

(58) Field of Classification Search
None
See application file for complete search history.

(56) References Cited

U.S. PATENT DOCUMENTS

| | | | |
|---|---|---|---|
| 5,696,379 | A | 12/1997 | Stock |
| 5,731,583 | A | 3/1998 | Bailey et al. |
| 5,834,777 | A | 11/1998 | Wong |
| 5,973,326 | A | 10/1999 | Parry et al. |
| 6,016,203 | A | 1/2000 | Martin |

(Continued)

FOREIGN PATENT DOCUMENTS

| | | |
|---|---|---|
| CN | 201203577 | 3/2009 |
| CN | 201716264 | 1/2011 |

(Continued)

OTHER PUBLICATIONS

PCT Application No. PCT/US2017/057793, International Search Report, dated Jan. 26, 2018, 5 pages.

(Continued)

*Primary Examiner* — Edwin Gunberg
(74) *Attorney, Agent, or Firm* — Wick Phillips Gould & Martin, LLP

(57) ABSTRACT

Embodiments relate generally to gas detector systems and method, wherein a gas detector system may comprise at least one emitter configured to emit radiation in a beam path; at least one detector configured to receive at least a portion of the emitted radiation, wherein the emitted radiation generates at least two focused spots at the at least one detector; a ring reflector configured to direct the emitted radiation around the ring reflector toward the at least one detector, wherein the ring reflector comprises at least a portion of a spheroid shape, and wherein the ring reflector is configured to allow gas to flow through at least a portion of the beam path; and a processing circuit coupled to the one or more detectors configured to processes an output from the one or more detectors.

19 Claims, 12 Drawing Sheets

(56) References Cited

U.S. PATENT DOCUMENTS

| | | | |
|---|---|---|---|
| 6,067,840 | A | 5/2000 | Chelvayohan et al. |
| 6,075,246 | A | 6/2000 | Stock |
| 6,121,617 | A | 9/2000 | Hirayama et al. |
| 6,194,735 | B1 | 2/2001 | Martin |
| 6,642,522 | B2 | 11/2003 | Clausen et al. |
| 6,650,417 | B2 | 11/2003 | Matthiessen |
| 6,753,967 | B2 | 6/2004 | Stuttard |
| 6,989,549 | B2 | 1/2006 | Dickmann et al. |
| 7,244,939 | B2 | 7/2007 | Stuttard |
| 7,268,882 | B2 | 9/2007 | Fischer et al. |
| 7,420,171 | B2 | 9/2008 | Hopkins et al. |
| 7,449,694 | B2 | 11/2008 | Yi et al. |
| 7,477,395 | B2 | 1/2009 | Dickmann et al. |
| 7,488,942 | B2 | 2/2009 | Hopkins et al. |
| 7,564,558 | B2 | 7/2009 | Martin |
| 7,609,375 | B2 | 10/2009 | Park |
| 7,876,443 | B2 | 1/2011 | Bernacki |
| 7,880,886 | B2 | 2/2011 | Ludwig |
| 8,193,502 | B2 | 6/2012 | Hodgkinson et al. |
| 8,368,895 | B2 | 2/2013 | Martin |
| 8,415,626 | B1 | 4/2013 | Wong |
| 8,471,208 | B1 | 6/2013 | Tang |
| 8,729,475 | B1 | 5/2014 | Wong |
| 8,760,655 | B2 | 6/2014 | Hayashi et al. |
| 8,796,629 | B2 | 8/2014 | Martin |
| 8,969,808 | B2 | 3/2015 | Henderson |
| 8,991,886 | B2 | 3/2015 | Schuster et al. |
| 9,035,256 | B2 | 5/2015 | Gibson et al. |
| 9,134,224 | B2 | 9/2015 | Matsushima et al. |
| 9,134,226 | B2 | 9/2015 | Nicoletti et al. |
| 9,234,837 | B2 | 1/2016 | Maksyutenko et al. |
| 9,297,758 | B2 | 3/2016 | Frigo |
| 2006/0086903 | A1 | 4/2006 | Hopkins et al. |
| 2008/0308733 | A1 | 12/2008 | Doncaster |
| 2009/0284745 | A1 | 11/2009 | Yi et al. |
| 2010/0208268 | A1* | 8/2010 | Haveri .................. G01N 21/05 356/437 |
| 2012/0261578 | A1* | 10/2012 | Scott .................. G01N 21/3504 250/339.07 |
| 2013/0162979 | A1 | 6/2013 | Chen et al. |
| 2014/0078494 | A1* | 3/2014 | Gidon .................. G01N 21/61 356/51 |
| 2015/0129767 | A1 | 5/2015 | Kouznetsov et al. |
| 2015/0219491 | A1 | 8/2015 | Lee et al. |
| 2016/0084747 | A1 | 3/2016 | Scott et al. |
| 2018/0120233 | A1 | 5/2018 | Marta et al. |

FOREIGN PATENT DOCUMENTS

| | | |
|---|---|---|
| CN | 102053063 | 5/2011 |
| CN | 202092949 | 12/2011 |
| CN | 102778441 | 11/2012 |
| CN | 202676593 | 1/2013 |
| CN | 103528957 | 1/2014 |
| CN | 103822892 | 5/2014 |
| CN | 103822893 | 5/2014 |
| CN | 103954577 | 7/2014 |
| CN | 104111226 | 10/2014 |
| CN | 104122223 | 10/2014 |
| CN | 104280357 | 1/2015 |
| CN | 104280358 | 1/2015 |
| CN | 204287035 | 4/2015 |
| DE | 102010050626 | 9/2012 |
| EP | 0647845 A1 | 4/1995 |
| GB | 2401679 | 6/2005 |
| JP | 9229858 | 9/1997 |
| JP | 10332585 | 12/1998 |
| JP | 2000019108 | 1/2000 |
| JP | 2007205920 | 8/2007 |
| JP | 2007333567 | 12/2007 |
| JP | 2008107337 | 5/2008 |
| JP | 4216110 | 11/2008 |
| JP | 2013002966 | 1/2013 |
| JP | 2014238307 | 12/2014 |
| JP | 5695301 | 4/2015 |
| JP | 5695302 | 4/2015 |
| JP | 2015152438 | 8/2015 |
| JP | 2015184211 | 10/2015 |
| KR | 10-0694635 | 3/2007 |
| KR | 10-0732708 | 6/2007 |
| KR | 10-0732709 | 6/2007 |
| KR | 10-0781968 | 12/2007 |
| KR | 2008-0076515 | 8/2008 |
| KR | 20090004271 | 1/2009 |
| KR | 20090086766 | 8/2009 |
| KR | 10-0996711 | 11/2010 |
| KR | 10-1026206 | 3/2011 |
| KR | 10-1026206 | 11/2011 |
| KR | 10-1088360 | 12/2011 |
| KR | 20130082482 | 7/2013 |
| WO | 02093141 A1 | 11/2002 |
| WO | 2010101430 | 9/2010 |
| WO | 2013105789 | 7/2013 |
| WO | 2016002467 | 1/2016 |
| WO | 2016002468 | 1/2016 |
| WO | 2018080956 A1 | 5/2018 |

OTHER PUBLICATIONS

PCT Application No. PCT/US2017/057793, Written Opinion of the International Searching Authoriday, dated Jan. 26, 2018, 8 pages.

\* cited by examiner

PLANAR REFLECTIVE RING

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Non-dispersive infrared (NDIR) detectors may typically comprise an IR source, a sample chamber (containing the gas sample), a sample detector, and a reference detector. The detectors may comprise optical bandpass filters depending on the target gas(s). The sample detector is used to detect the target gas and the reference detector is used to ignore the target gas and any known interferrants. The reference detector provides a base point or zero while the sample detector provides the signal with the differential providing the actual span value of the instrument. This sample/reference approach compensates for the changes that can occur in the detector sensitivity or source. For example, the source intensity can change due to contamination causing a zero drift.

It is a common safety practice to use two detectors with a means of selecting different wavelength bands of the source light. For example, the reference signal can be used in conjunction with the sample signal to determine any drop in the intensity of the radiation output, any loss of intensity due to fouling of the detector (e.g., a fogged or dirty window, etc.), or any substances in the light path that may affect the intensity of the radiation (e.g., dust, water vapor, etc.). The reference detector can also be used to ensure that radiation is being received. If the reference detector does not have a signal, then an indication that the radiation is not present may be generated. This may help ensure that the system is operating. In comparison, a zero response in a prior system may simply be interpreted as a lack of the presence of a target gas when in fact the light source is not working. The reference signal can be used to compensate the detected signal from the sample detector to produce a response with an improved accuracy.

SUMMARY

In an embodiment, a gas detector system may comprise at least one emitter configured to emit radiation in a beam path; at least one detector configured to receive at least a portion of the emitted radiation; a ring reflector configured to direct the emitted radiation around the ring reflector toward the at least one detector, wherein the ring reflector comprises at least a portion of a spheroid shape, and wherein the ring reflector is configured to allow gas to flow through at least a portion of the beam path; and a processing circuit coupled to the one or more detectors configured to processes an output from the one or more detectors.

In an embodiment, a method for gas detection may comprise generating a beam path of emitted radiation by an emitter; directing the beam path of emitted radiation within a ring reflector through a gas sample; reflecting the beam path of emitted radiation around the ring reflector toward a detector, wherein the ring reflector comprises at least a portion of a spheroid shape; receiving the beam path of emitted radiation by the detector; and determining the at least one gas concentration of the gas sample based on the received beam path of emitted radiation.

In an embodiment, a gas detector system may comprise at least one emitter configured to emit radiation in a beam path; at least one detector configured to receive at least a portion of the emitted radiation, wherein the emitted radiation generates at least two focused spots at the at least one detector; a ring reflector configured to direct the emitted radiation around the ring reflector toward the at least one detector, wherein the ring reflector comprises at least a portion of a spheroid shape, and wherein the ring reflector is configured to allow gas to flow through at least a portion of the beam path; and a processing circuit coupled to the one or more detectors configured to processes an output from the one or more detectors.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
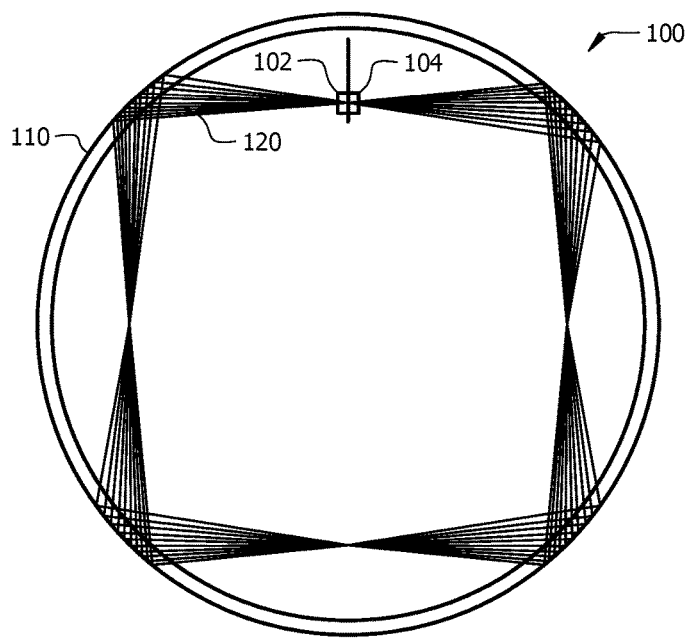
FIG. 1A illustrates a front view of a ring reflector according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for improving response time in a gas detector. The gas detector may comprise a spheroid ring reflector configured to direct radiation from an emitter to at least one detector, wherein the path-length of the radiation may be determined by the circumference of the ring reflector.

Certain applications for gas detectors (such as handheld, portable, and wireless, as well as fixed location) may require low profile, thin, small gas detectors. However, a certain path-length may be required for efficient detection, particularly in an optical NDIR gas sensor. Additionally, large cross-sectional areas for gas exchange ports are desirable to allow for improved response time of the sensor.

As described above, NDIR detectors may typically comprise an IR source, a sample chamber (containing the gas sample), a sample detector, and a reference detector. The IR source may be modulated. The detectors may comprise optical bandpass filters depending on the target gas(s). The sample detector is used to detect the target gas and the reference detector is used to ignore the target gas and any known interferrants. The reference detector provides a base point or zero while the sample detector provides the signal with the differential providing the actual span value of the instrument. This sample/reference approach compensates for the changes that can occur in the detector sensitivity or source. For example, the source intensity can change due to contamination causing a zero drift.

It is a common safety practice to use two detectors with a means of selecting different wavelength bands of the source light. For example, the reference signal can be used to determine any drop in the intensity of the radiation output, any loss of intensity due to fouling of the detector (e.g., a fogged or dirty window, etc.), or any substances in the light path that may affect the intensity of the radiation (e.g., dust, water vapor, etc.). The reference detector can also be used to ensure that radiation is being received. If the reference detector does not have a signal, then an indication that the radiation is not present may be generated. This may help ensure that the system is operating. In comparison, a zero response in a prior system may simply be interpreted as a lack of the presence of a target gas when in fact the light source is not working. The reference signal can be used to compensate the detected signal from the sample detector to produce a response with an improved accuracy.

Figure 1B:
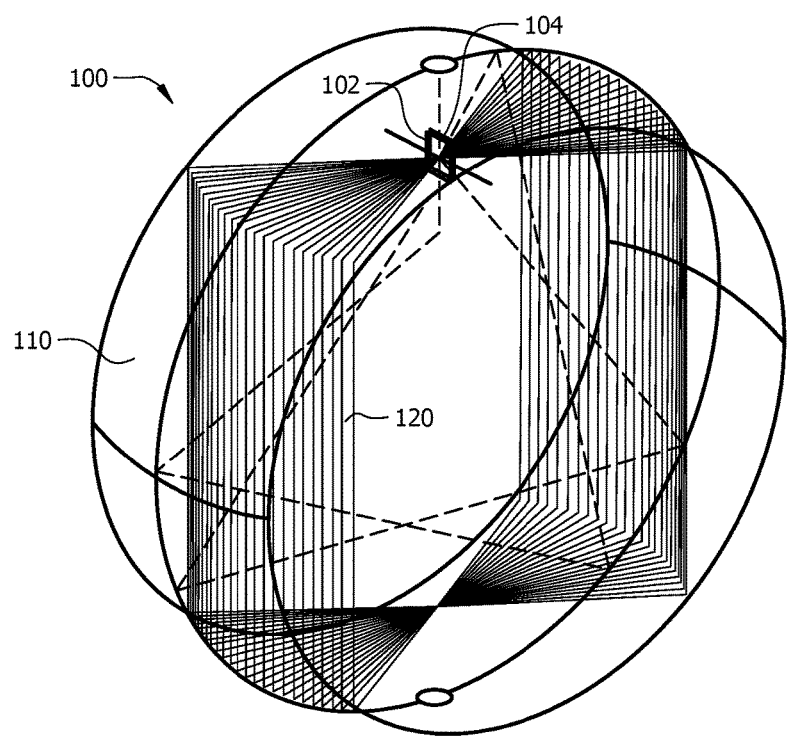
FIG. 1B illustrates a perspective view of a ring reflector according to an embodiment of the disclosure.

Referring now to FIGS. 1A-1B, an exemplary spheroid ring reflector 100 is shown. The spheroid ring reflector 100 comprises an emitter 102 (or radiation source) configured to emit radiation, which may for example comprise infrared (IR) radiation and/or a light emitting diode (LED). In some embodiments, the emitter 102 may be modulated. The spheroid ring reflector 100 may also comprise a detector 104 configured to receive the emitted radiation. In some embodiments, the spheroid ring reflector 100 may comprise curved walls 110, wherein the beam path 120 from the emitter 102 may reflect off of the curved walls 110 and be directed toward the detector 104. The curved walls 110 may "contain" the beam path 120 within the spheroid ring reflector 100, allowing for focusing of the beam path 120 toward the detector 104, and preventing continuous expansion of the beam path 120. In the embodiment shown in FIG. 1, the emitter 102 and detector 104 may be oriented "back to back." However, other orientations for the emitter 102 and detector 104 may also be used.

In use, a gas may be passed through the spheroid ring reflector 100 while the radiation is being directed from the emitter 102 toward the detector 104. In some embodiments, the detector 104 may comprise one or more filters for a target wavelength and/or a reference wavelength. In some embodiments, the emitter 102 may comprise one or more filters, and/or a plurality of filters may be used within the spheroid ring reflector 100. The detection of the target wavelength may be correlated to the presence and/or amount of a target gas within the gases that are passed through the spheroid ring reflector 100. As an example, the gases passing through the spheroid ring reflector 100 may comprise flammable gasses, hydrocarbons, CO and/or $CO_2$, among other things.

In some embodiments, different methods may be used to fan the beam path 120 from the emitter 102 toward the curved walls 110. For example, in FIG. 1A, a y-axis fan may be used. As another example, in FIG. 1B, an x-axis fan may be used. The fanning methods may provide various benefits for the control of the beam path 120 within the spheroid ring reflector 100.

Figure 2A:
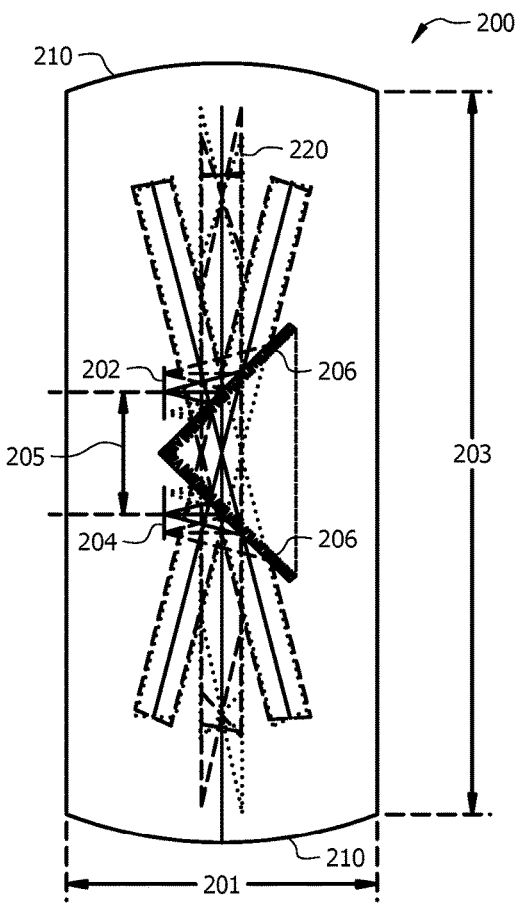
FIG. 2A illustrates a side view of a ring reflector according to an embodiment of the disclosure.
Figure 2B:
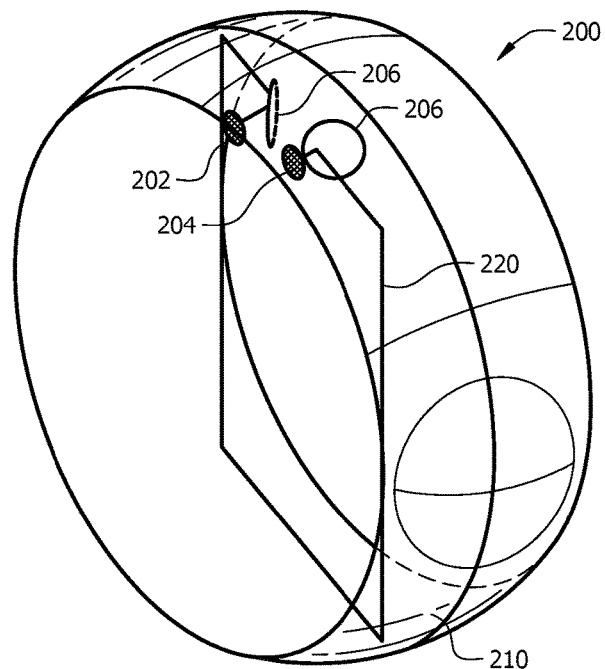
FIG. 2B illustrates a perspective view of a ring reflector according to an embodiment of the disclosure.

FIGS. 2A-2B illustrate a spheroid ring reflector 200, which may be similar to the spheroid ring reflector 100 described above. In the embodiment shown in FIGS. 2A-2B, the emitter 202 and detector 204 may be mounted on the same surface, side by side. The spheroid ring reflector 200 comprises one or more reflectors 206 configured to direct the radiation from the emitter 202 and toward the detector 204. In some embodiments the reflectors 206 may be a part of a right angle prism. In some embodiments, the reflectors 206 may comprise mirrors. In some embodiments, the reflectors 206 may be incorporated directly into the spheroid ring reflector 200, wherein the reflectors 206 may comprise the same material as the curved walls 210.

Locating the emitter 202 and detector 204 in the same plane, as shown in FIGS. 2A-2B, may allow for the spheroid ring reflector 200 to have a reduced thickness (or profile). The beam path 220 may be contained within the curved walls 210 of the ring reflector 200. In some embodiments, the distance 205 between the emitter 202 and detector 204 may be approximately 3 millimeters (mm). In some embodiments, the emitter 202 may comprise a 1 mm by 1 mm emitter. In some embodiments, the detector 204 may comprise a 1 mm by 1 mm detector. In some embodiments, the spheroid ring reflector 200 may comprise a diameter of approximately 20 mm. These measurements and dimensions may be exemplary, and other dimensions for the emitter, detector, and ring diameter may also be used.

In some embodiments, as shown in FIGS. 2A-2B, multiple wavelengths of radiation may be emitted by the emitter 202. In other embodiments, a single wavelength, or small range of wavelengths may be emitted by the emitter 202. In some embodiment, the direction and angle of the beam path 220 may be controlled by the orientation of the reflectors 206. The beam path 220 may be controlled such that the beam path 220 is focused at the detector 204.

Making use of the curved inner surface of the spheroid ring reflector 200, the optical path-length of the beam path 220 may be approximately the circumference of the inner diameter 203 of the ring. The reflected radiation beam path 220 may be confined to the inner ring width 201 due to the imaging properties of the spheroid ring reflector 200, thus allowing the two sides of the spheroid ring reflector 200 to be completely open, thereby providing a large cross-sectional area for gas exchange and flow through. The spheroid ring reflector 200 may comprise a 1 to 1 imager to the 1st order and thus the detector 204 may be the same size as the emitter 202. Because the beam path 220 is contained by the spheroid ring reflector 200, there is no need for a top or bottom reflecting surface to confine the radiation and this reduces the number of required elements.

It may be desired to minimize the size of a gas detector, and therefore a spheroid ring reflector 200. The inner ring width 201 of the spheroid ring reflector 200 may be optimized based on throughput efficiency from the emitter 202 to the detector 204, wherein a positive linear relationship exists between the inner ring width 201 and the throughput efficiency. Similarly, the inner diameter 203 of the spheroid ring reflector 200 may be optimized based on throughput efficiency as well as path-length of the beam path 220, wherein a negative relationship exists between the inner ring diameter 203 and the throughput efficiency, but path-length should be maximized. In some embodiments, the inner ring diameter 203 of the inner ring of the spheroid reflector ring 200 may be approximately 20 mm. In some embodiments, the path length for the beam path 220 (from the emitter 202 to the detector 204) may be at least approximately 50 mm. In some embodiments, the path length for the beam path 220 may be approximately 56 mm. In some embodiments, the inner ring width 201 of the spheroid ring reflector 200 may be approximately 8 mm. In some embodiments, the inner ring width 201 of the spheroid ring reflector 200 may be between approximately 5 mm and 10 mm.

FIG. 2B illustrates a perspective view of the spheroid ring reflector 200. The emitter 202 and detector 204 may be located on one side of the spheroid ring reflector 200. The beam path 220 may be directed within the spheroid ring reflector 200 using the reflectors 206.

Figure 3:
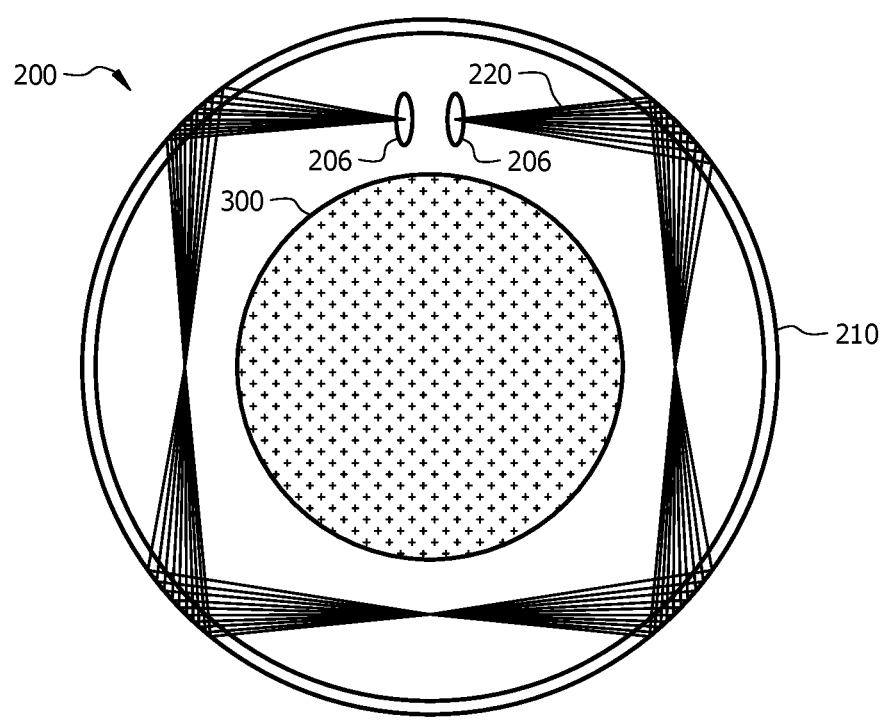
FIG. 3 illustrates a front view of a ring reflector comprising a central plug according to an embodiment of the disclosure.

FIG. 3 illustrates a spheroid ring reflector 200 comprising a central plug 300 located within the center space of the spheroid ring reflector 200. The center space within the spheroid ring reflector 200 may be referred to as "dead space" because the beam path 220 does not pass through that area. Therefore, when a gas is passed through the spheroid ring reflector 200, the gas that passes through the dead space may not interact with any of the beam path 220 and may be wasted, contributing to a slower response time. A central plug 300 may block the central dead space and direct the gas to flow through the areas where the beam path 220 is located, preventing wasting of the gas flowing through the spheroid ring reflector 200. The central plug 300 may also provide other effects on the gas flow (or may provide airflow control), such as a chimney effect. In some embodiments, the dead space may also be used to place other elements for an assembled gas sensor, such as electrical components.

In some embodiments, the emitter 202 and detector 204 could possibly be mounted side by side, back to back, opposing sides, or in another orientation. The radiation from the emitter 202 may be directed toward the detector 204 using the spheroid ring reflector 200 itself as well as optionally other reflector elements.

Figure 4A:
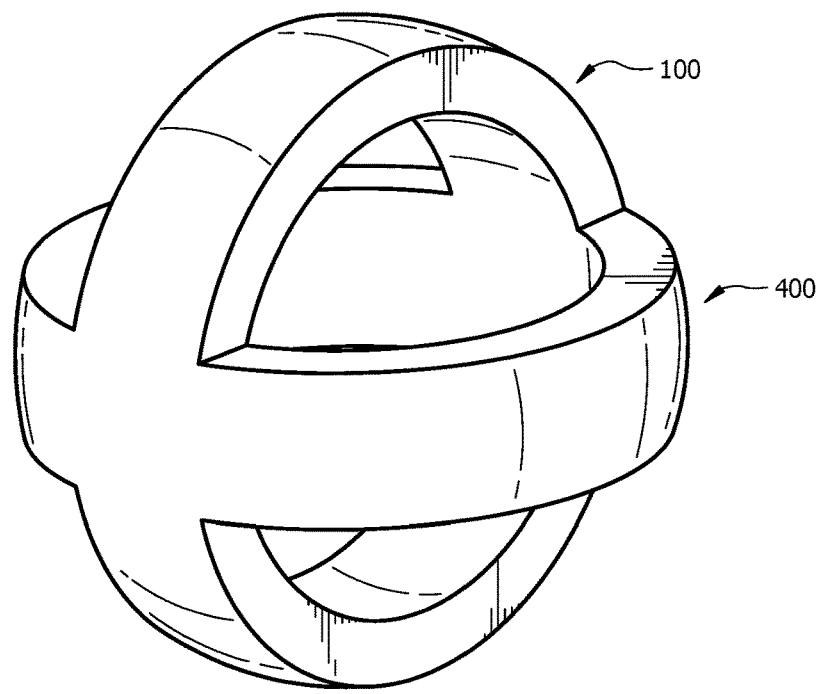
FIGS. 4A-4B illustrate perspective views of a ring reflector according to an embodiment of the disclosure.
Figure 4B:
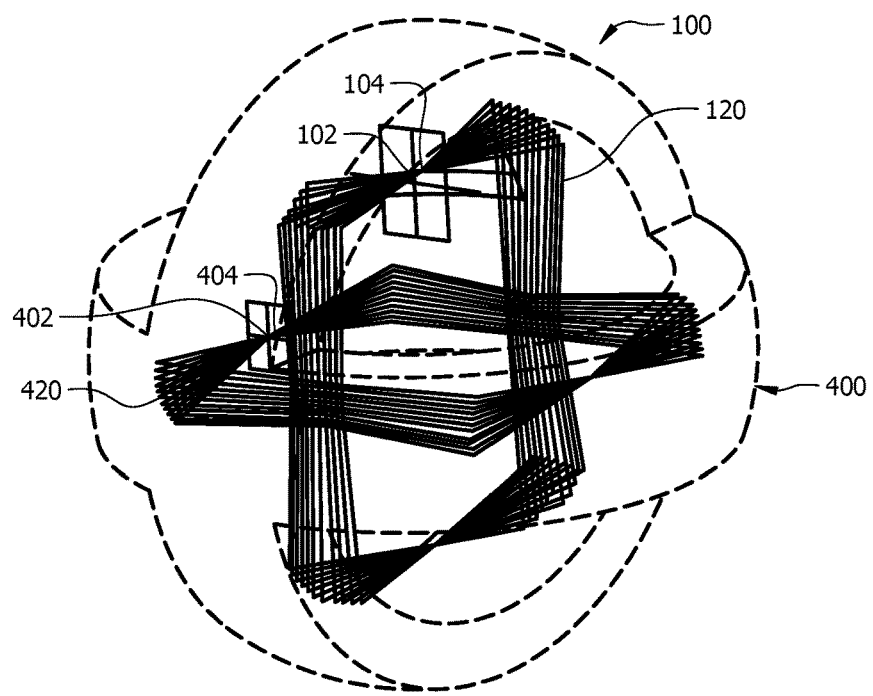

FIGS. 4A-4B illustrate a perspective view of the spheroid ring reflector 100, wherein the spheroid ring reflector 100 further comprises a second channel 400 comprising a second emitter 402, a second detector 404, and a second beam path 420. The second beam path 420 may be oriented such that the second beam path 420 does not interfere with the first beam path 120. In some embodiments, the second beam path 420 may be oriented at some angle to the first beam path 120. In the embodiment shown in FIGS. 4A-4B, the second beam path 420 may be orthogonal to the first beam path 120, but in other embodiments, the beam paths may be oriented at another angle to one another.

Figure 5:
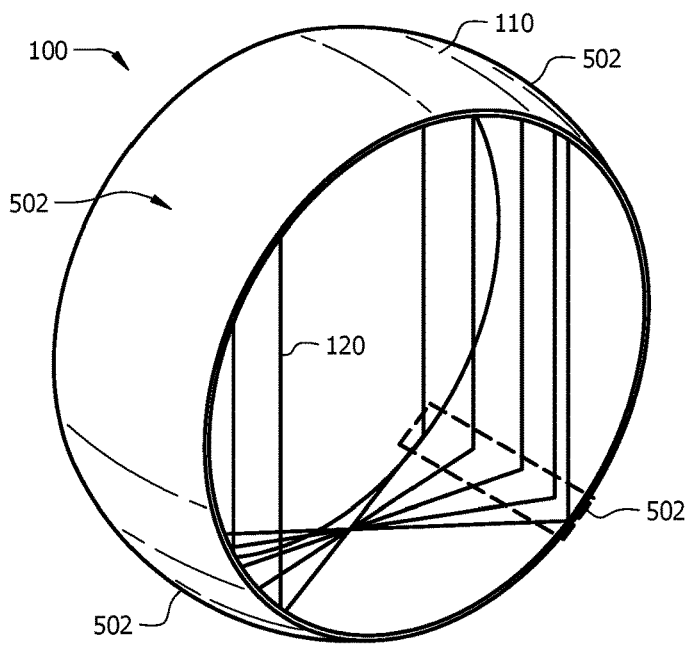
FIG. 5 illustrates another perspective view of a ring reflector according to an embodiment of the disclosure.

As shown in FIG. 5, in some embodiments, there may be certain areas 502 of the curved walls 110 where the radiation is more focused on the surface of the curved walls 110. For example, at the four corners of the beam path 120, the intensity of the radiation may be higher than in other areas of the curved walls 110. In some embodiments, the areas of the curved wallsl that do not have a high intensity of radiation may be used for other purposes, such as locating other elements, electrical components, condensation removal elements, among other things.

Figure 6:
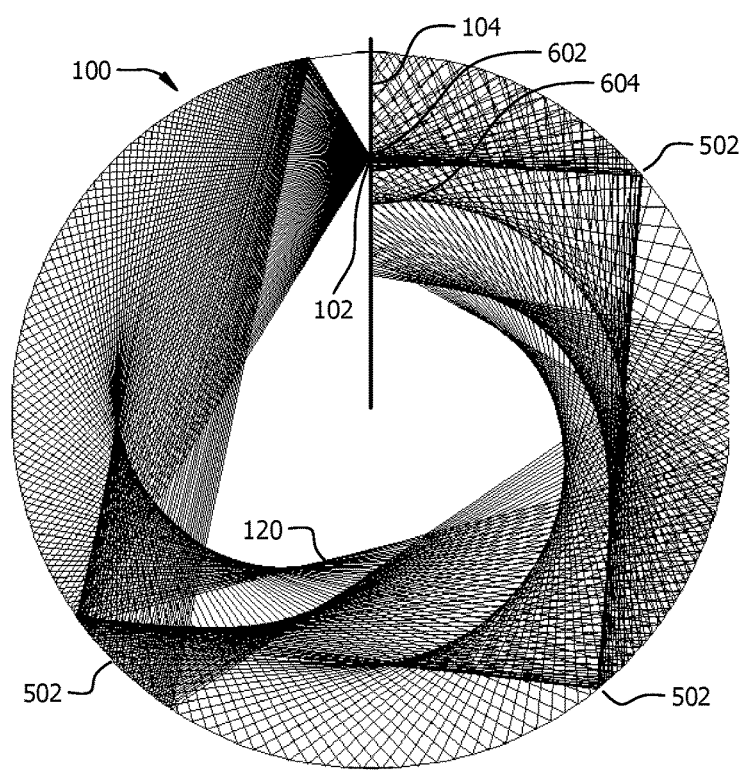
FIG. 6 a detailed view of the light paths within a ring reflector according to an embodiment of the disclosure.

Referring to FIG. 6, the confinement of the beam path 120 along the central plane of the spheroid ring reflector 100 may generate a secondary focus due to propagation around the ring of larger emission angle from the emitter, known as astigmatism aberration, wherein the radiance of the radiation may be focused in two spots within the spheroid ring reflector 100. A first focused spot (or location) 602 may be used to locate the detector 104 (as described above) while the second focused spot (or location) 604 may serve as a reference location for a reference detector. In other words, the spheroid ring reflector 100 may utilize the intrinsic defect caused by the astigmatism aberration to provide two focused spots 602 and 604 without the need for additional optics (such as a bi-mirror or diffractive element), thereby saving space and cost for the spheroid ring reflector 100. Directing two separate beams at the detector 104 is advantageous to provide a sample signal and a reference signal. In some embodiments, both of the two "spots" (or signals) 602 and 604 may be received by the detector 104, wherein the detector 104 may comprise a "sample signal" portion and a "reference signal" portion. In another embodiment, multiple detectors 204 may be located within the spheroid ring reflector 100.

In some embodiments, the multiple focused spots 602 and 604 may comprise different intensities. In some embodiments, the lower intensity spot may be used for the reference detector and the higher intensity spot may be used for the sample detector. Alternatively, the lower intensity spot may be used for the sample detector and the higher intensity spot may be used for the reference detector.

FIGS. 7A-7D illustrate a spheroid ring reflector 700 that may be similar to the spheroid ring reflector 200, where the emitter 702 and detector 704 are located on opposing sides of the spheroid ring reflector 700, and a not located within the same plane. The beam path 720 may be directed from the emitter 702, toward walls 710 of the spheroid reflector ring 700, and toward the detector 704 by one or more reflectors 706 located within the spheroid reflector ring 700. The beam path 720 may be similar to the beam path 220 described above. In some embodiments, the reflectors 706 may comprise parallel reflectors. In some embodiments, the spheroid ring reflector 700 may comprise at least one filter 740 located such that the beam path 720 passes through the filter 740 before reaching the detector 704. The filter 740 may be configured to filter one or more wavelengths.

In some embodiments, the emitter 702 may comprise an LED with a package diameter of approximately 5.2 mm. In some embodiments, the detector 704 may comprise a package diameter of approximately 5.2 mm. In some embodiments, the center of the spheroid ring reflector 700 may be hollow through the center.

Figure 7A:
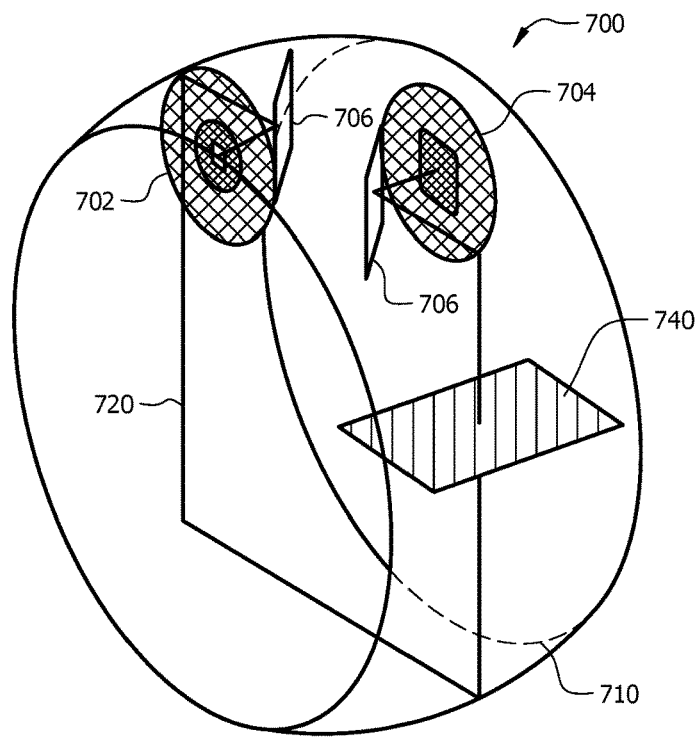
FIG. 7A illustrates a perspective view of a ring reflector according to an embodiment of the disclosure.
Figure 7B:
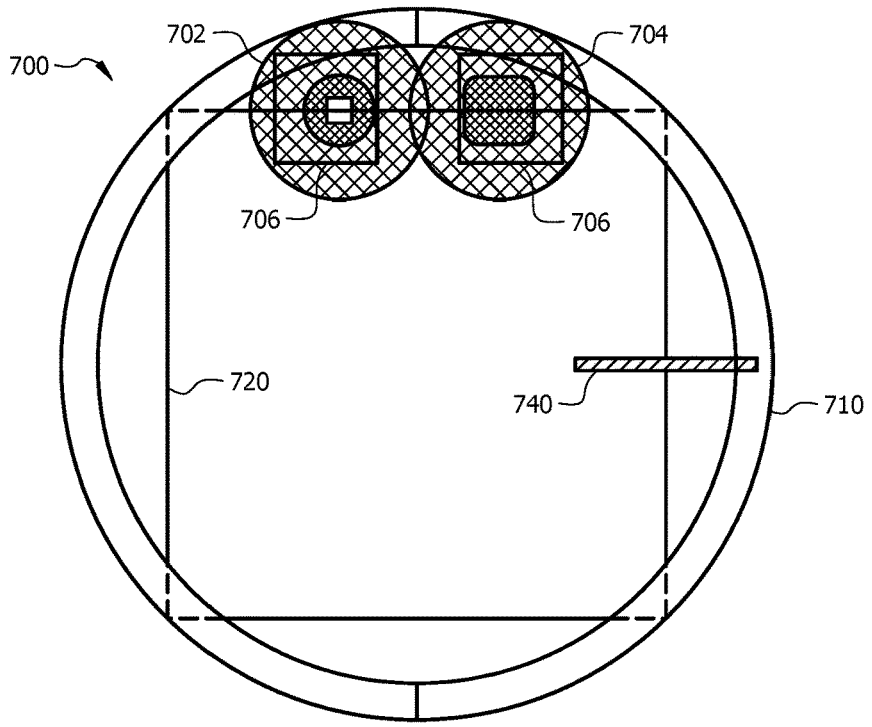
FIG. 7B illustrates a front view of the ring reflector of FIG. 7A according to an embodiment of the disclosure.
Figure 7C:
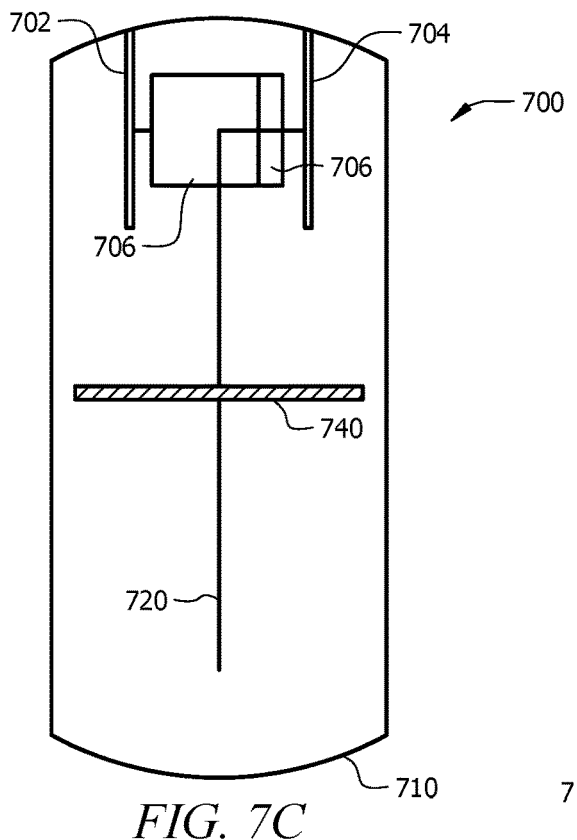
FIG. 7C illustrates a side view of the ring reflector of FIG. 7A according to an embodiment of the disclosure.
Figure 7D:
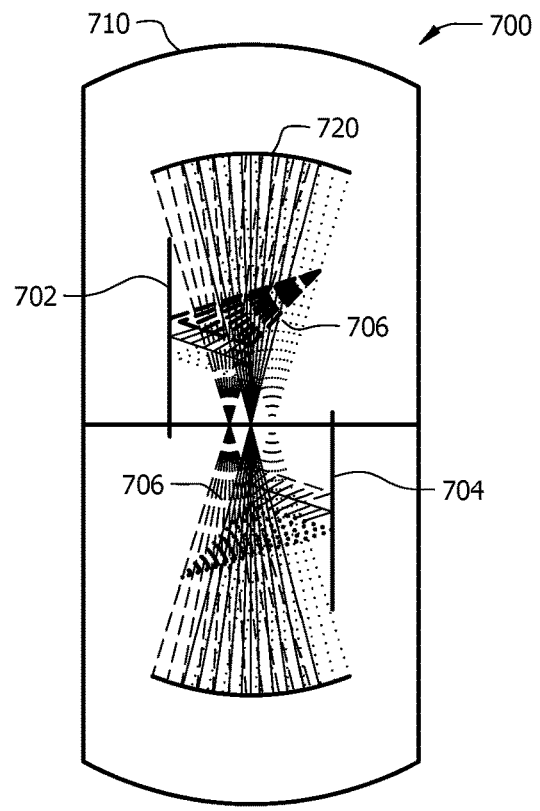
FIG. 7D illustrates a top view of the ring reflector of FIG. 7A according to an embodiment of the disclosure.

As shown in FIG. 7B, the emitter 702 and detector 704 may be located in different planes (and not side by side) because the size and location of the emitter 702 and detector 704 packages would cause them to overlap. By locating the emitter 702 and detector 704 in different planes, the size may not be as constrained as when they are located in the same plane.

Figure 8:
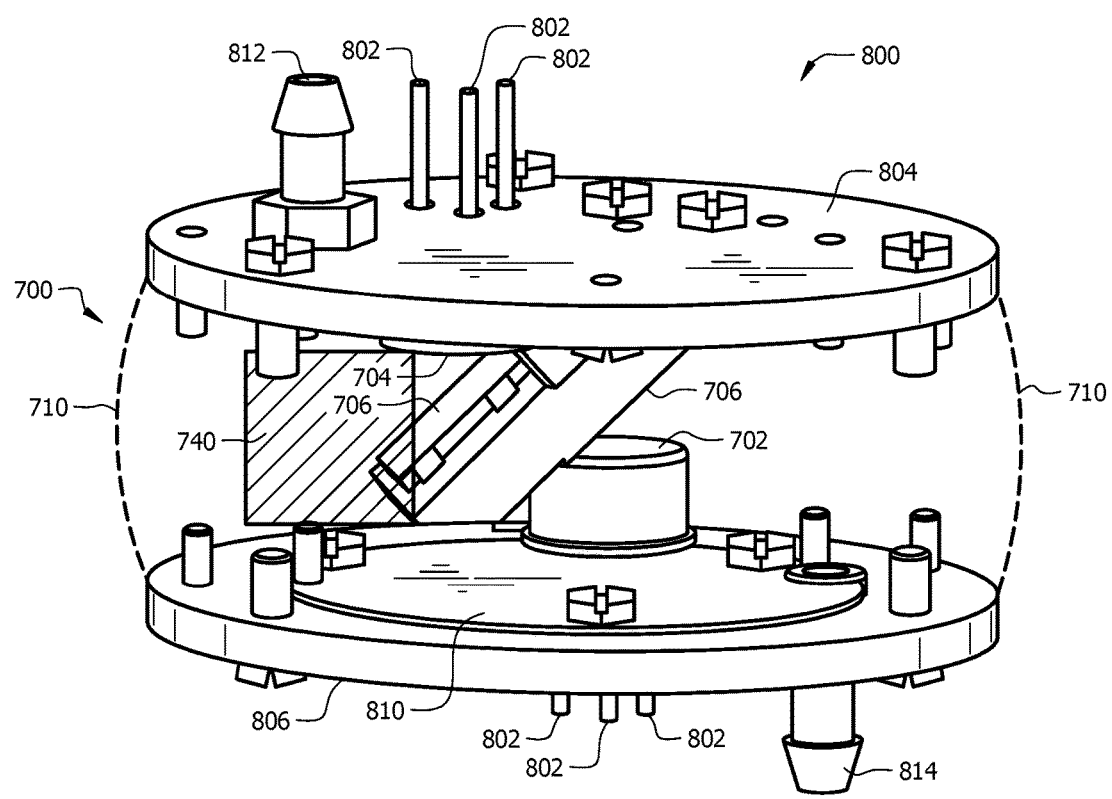
FIG. 8 illustrates a detector comprising a ring reflector according to an embodiment of the disclosure.

FIG. 8 illustrates a detector 800 in which a spheroid ring reflector 700 may be used. The walls 710 of the spheroid ring reflector 700 are transparent to show the internal components. The detector 800 may comprise a top plate 804 and a bottom plate 806 comprising additional components. In some embodiments, the emitter 702 may be mounted on the bottom plate 806 and the detector 704 may be mounted on the top plate 804. In some embodiments, the reflectors 706 may be located between the top plate 804 and bottom plate 806. In some embodiments, the emitter 702 and detector 704 may be attached to leads 802 which may allow for controlling inputs and outputs to/from the emitter 702 and detector 704. In some embodiments, the detector 800 may comprise a processing circuit 810 (which may be one or more printed circuit boards). In some embodiments, the detector 800 may comprise a gas inlet 812 and a gas outlet 814, wherein the gas may pass through the spheroid ring reflector 700.

Figure 9:
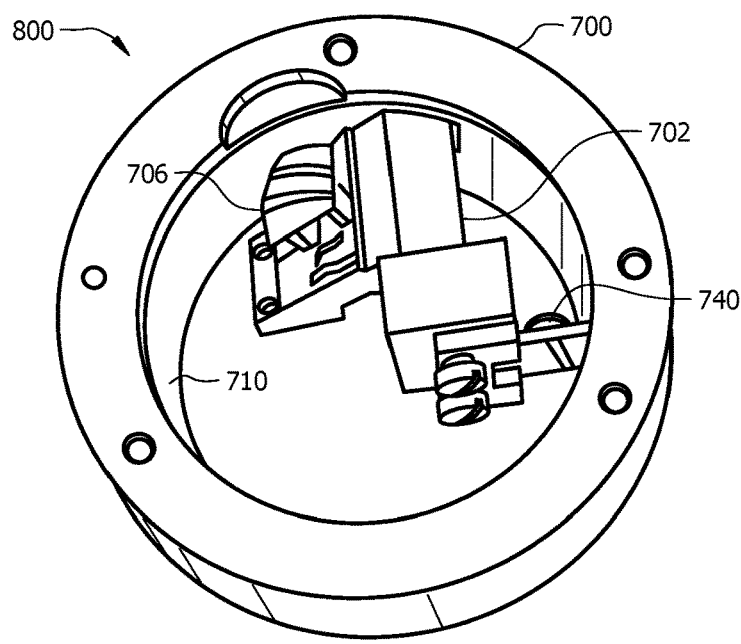
FIG. 9 illustrates another view of a detector comprising a ring reflector according to an embodiment of the disclosure.
Figure 10:
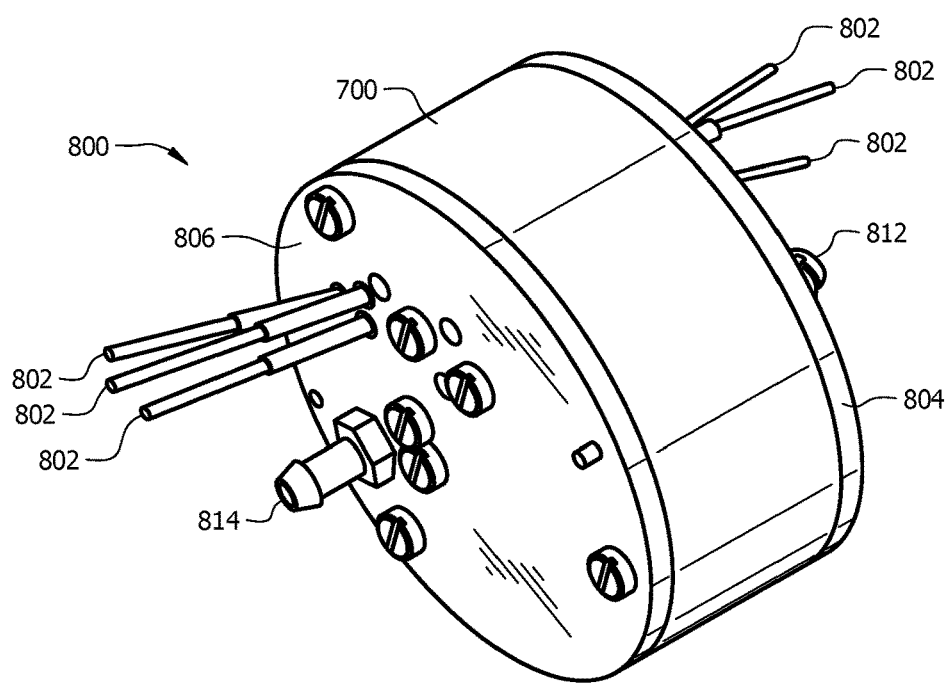
FIG. 10 illustrates yet another view of a detector comprising a ring reflector according to an embodiment of the disclosure.

FIGS. 9 and 10 illustrate additional views of the detector 800. In FIG. 9, the top plate 804 is attached to the spheroid ring reflector 700. In FIG. 10, the detector 800 is assembled with both the top plate 804 and bottom plate 806. Additionally, the filter 740 may be located such that the filter 740 is removable, wherein the filter 740 may be interchanged to complete testing with multiple filters. In an alternative embodiment, the filter 740 may be more permanently incorporated into the detector 800.

In some embodiments, the spheroid ring reflector 700 may comprise an acrylic material. In some embodiments, the spheroid ring reflector 700 may comprise a copper material. In some embodiments, the spheroid ring reflector 700 may comprise any suitable reflective material. The ring could be made of many materials, where the material may be processed to improve the quality of the surface finish on the interior of the ring and the reflectivity of the surface. In some embodiments, a reflective coating may be applied to the ring (such as gold or chrome) that will enable the light to be reflected efficiently from the surface, and may be selected based on wavelength and performance.

In FIGS. 8-10, the spheroid ring reflector 700 is shown assembled within a detector device. However, in other embodiments, the spheroid ring reflector 100, 200, and/or 700 may be installed within an open pipe, wherein there is no need for top or bottom plates to contain the emitted radiation from the emitter.

Figure 11A:
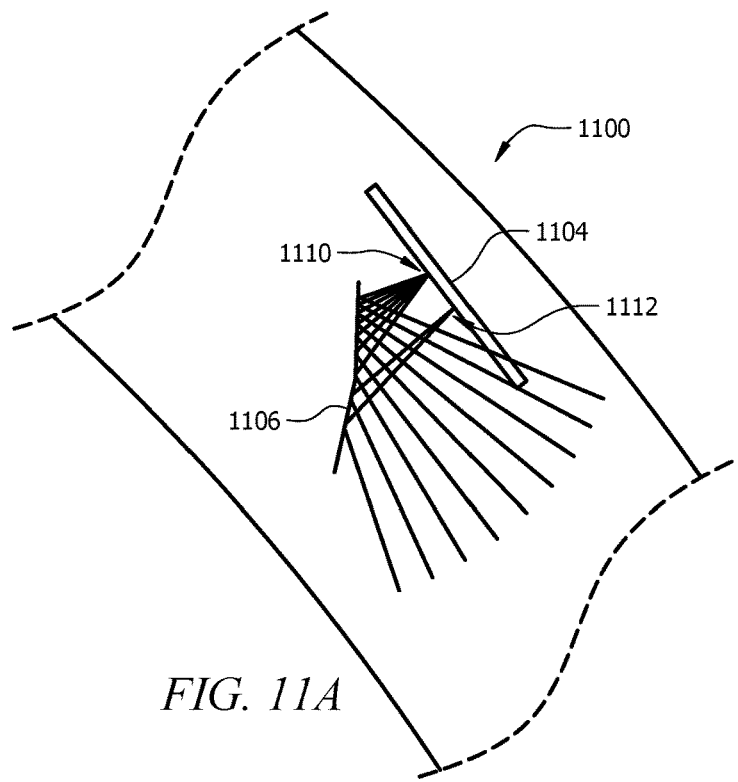
FIGS. 11A-11B illustrate detailed views of a detector and reflector(s) according to an embodiment of the disclosure.
Figure 11B:
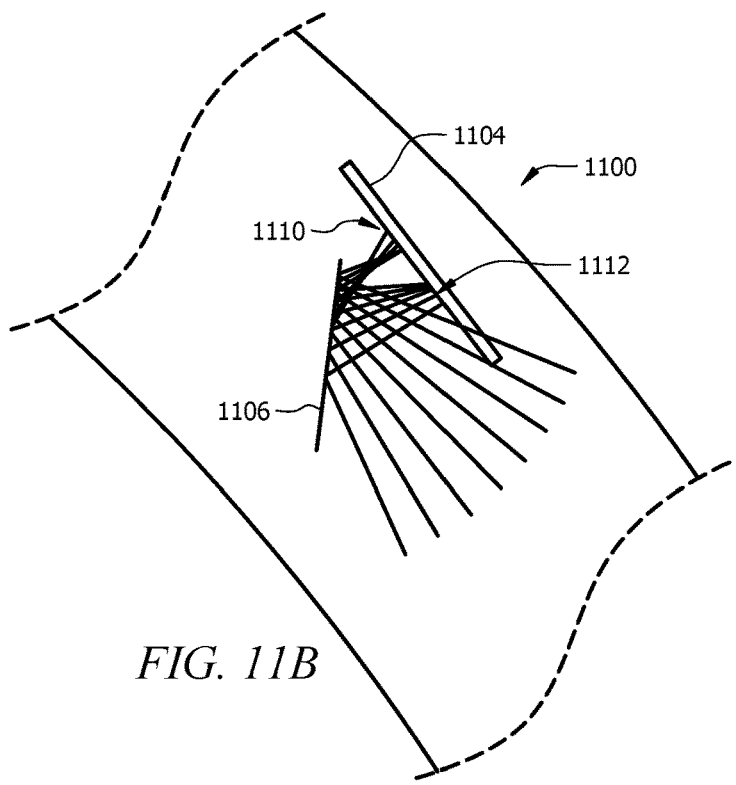

Referring to FIGS. 11A-11B a detailed view of a detector 1104 and reflector 1106 within a spheroid ring reflector 1100 is shown. The detector 1104 may be similar to the detectors 104, 204, 704 described above. In some embodiments, the reflector 1106 may be configured to control the two focused spots 1110 and 1112 generated by the emitted radiation. In FIG. 11A, it may be desired to provide more separation between the two focused spots 1110 and 1112, and therefore a bi-mirror may be used as a reflector 1106. In FIG. 11B, it may be desired to provide approximately equal intensities for the two focused spots 1110 and 1112, and therefore a diffractive grating may be used as a reflector 1106. FIGS. 11A-11B illustrate examples of controlling the two focused spots 1110 and 1112 with the reflector 1106, but other variations may also be used. In some embodiments, the reflector 1106 may be chosen or designed to generate a single focused spot on the detector 1104.

Figure 12:
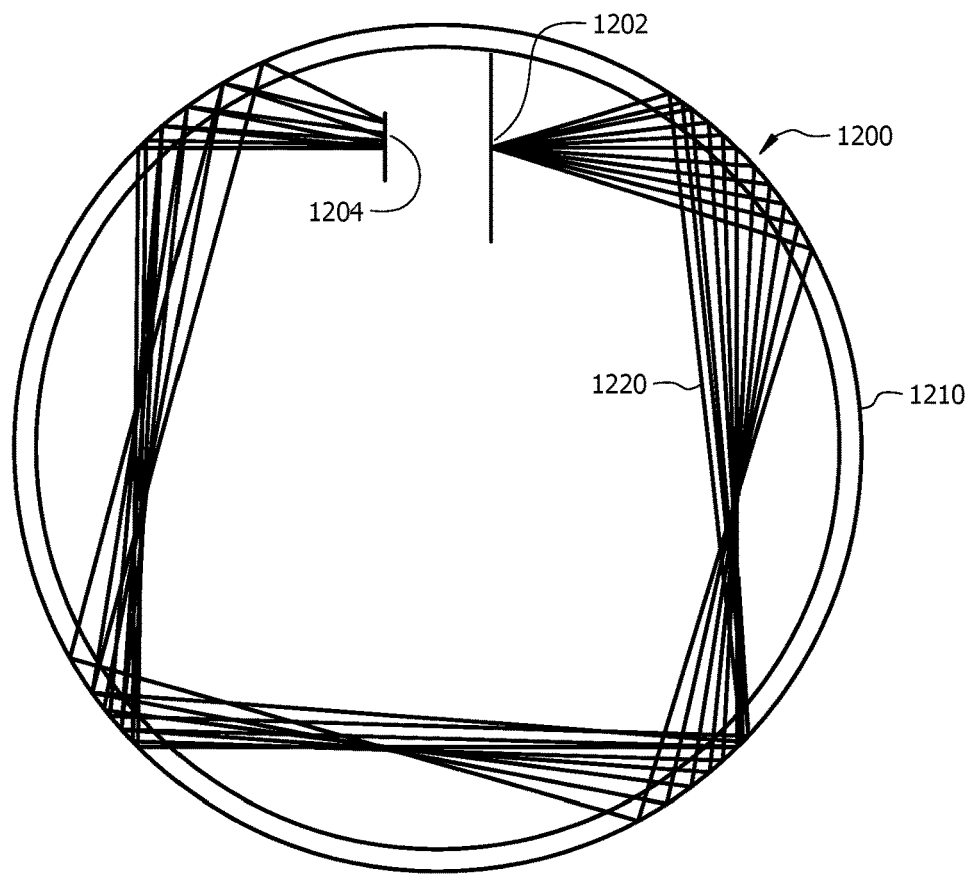
FIG. 12 illustrates a front view of a ring reflector according to an embodiment of the disclosure.

Referring to FIG. 12, another embodiment of a spheroid ring reflector 1200 is shown, comprising an emitter 1202 and a detector 1204, wherein the beam path 1220 from the emitter 1202 reflects off of the curved walls 1210 of the spheroid ring reflector 1200 toward the detector 1204. FIG. 12 illustrates how the beam path 1220 may generate more than one focused spot at the detector 1204 due to spreading of the beam path 1220.

Figure 13A:
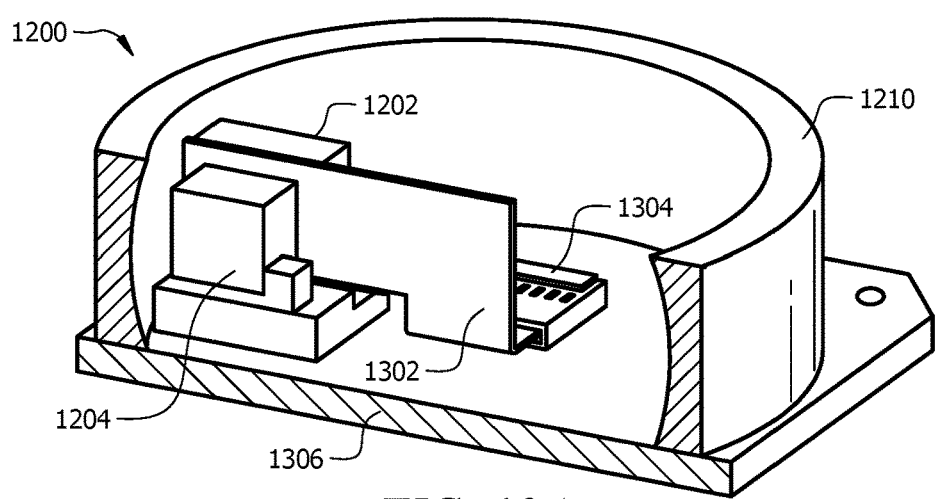
FIGS. 13A-13B illustrate views of a ring reflector assembled with electrical elements according to an embodiment of the disclosure.
Figure 13B:
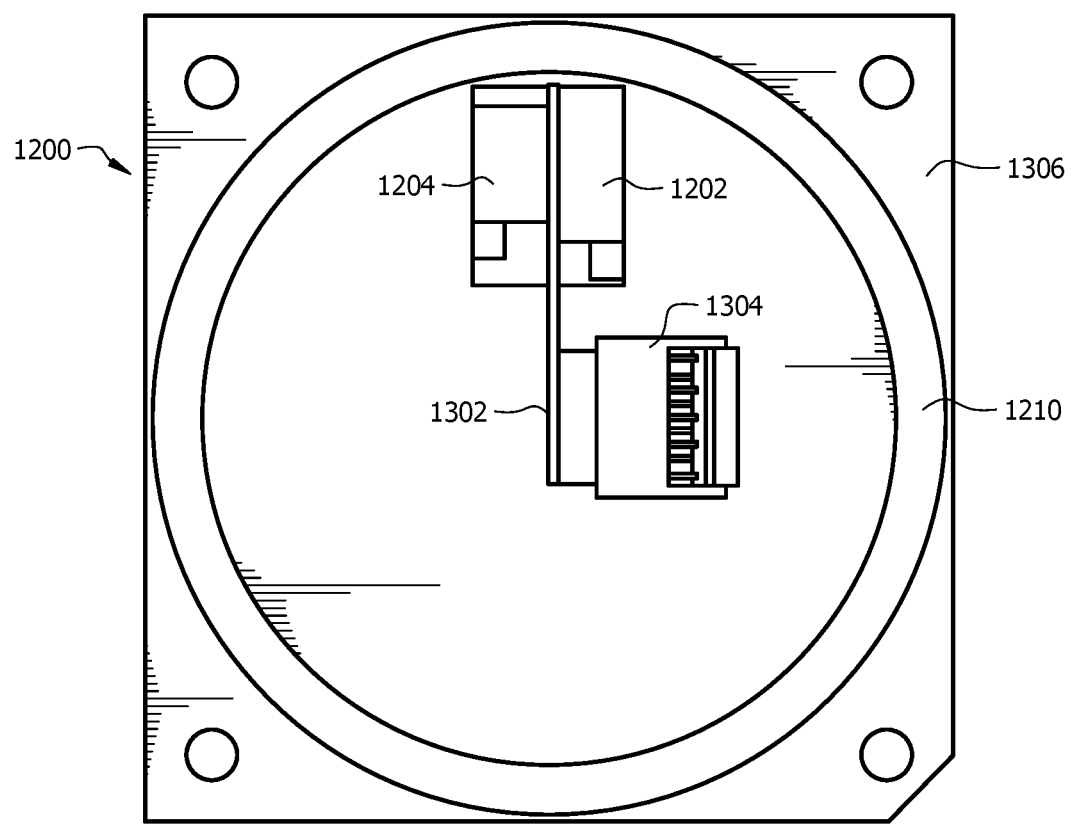

FIGS. 13A-13B illustrate the ring reflector 1200 assembled with electrical components, including a printed circuit board (PCB) 1306. The emitter 1202 and detector 1204 may be attached to one or more connectors 1302 and 1304 configured to allow communication between the emitter 1202, detector 1204 and the PCB 1306. As described above, one or more of the connectors 1302 and 1304 may be located within the central dead space of the ring reflector 1200.

In a first embodiment, a gas detector system may comprise at least one emitter configured to emit radiation in a beam path; at least one detector configured to receive at least a portion of the emitted radiation; a ring reflector configured to direct the emitted radiation around the ring reflector toward the at least one detector, wherein the ring reflector comprises at least a portion of a spheroid shape, and wherein the ring reflector is configured to allow gas to flow through at least a portion of the beam path; and a processing circuit coupled to the one or more detectors configured to process an output from the one or more detectors.

A second embodiment can include the gas detector system of the first embodiment, further comprising one or more reflectors configured to direct the beam path from the emitter toward a wall of the ring reflector.

A third embodiment can include the gas detector system of the first or second embodiments, further comprising one or more reflectors configured to direct the beam path toward the at least one detector.

A fourth embodiment can include the gas detector system of the third embodiment, wherein the one or more reflectors comprises a right angle prism.

A fifth embodiment can include the gas detector system of the third or fourth embodiments, wherein the one or more reflectors comprises two parallel mirrors.

A sixth embodiment can include the gas detector system of any of the first to fifth embodiments, wherein the emitted radiation generates at least two focused spots at the at least one detector.

A seventh embodiment can include the gas detector system of the sixth embodiment, wherein a first focused spot is used for a sample signal and a second focused spot is used for a reference signal.

An eighth embodiment can include the gas detector system of any of the first to seventh embodiments, wherein the emitter and the detector are oriented side by side in the same plane.

A ninth embodiment can include the gas detector system of any of the first to eighth embodiments, wherein the emitter and the detector are oriented opposite one another within the ring reflector in different planes.

A tenth embodiment can include the gas detector system of any of the first to ninth embodiments, further comprising at least one filter located such that the emitted radiation passes through the filter before reaching the detector.

An eleventh embodiment can include the gas detector system of any of the first to tenth embodiments, further comprising a second emitter configured to emit radiation in a second beam path; and a second detector configured to receive at least a portion of the emitted radiation in the second beam path, wherein the second beam path is oriented at an angle to the first beam path.

A twelfth embodiment can include the gas detector system of any of the first to eleventh embodiments, further comprising a plug configured to minimize gas flow through dead space within the ring reflector.

A thirteenth embodiment can include the gas detector system any of the first to twelfth embodiments, wherein the ring reflector comprises a diameter between approximately 10 and 20 millimeters.

A fourteenth embodiment can include the gas detector system of any of the first to thirteenth embodiments, wherein the ring reflector comprises a width between approximately 5 millimeters and 10 millimeters.

In a fifteenth embodiment, a method for gas detection may comprise generating a beam path of emitted radiation by an emitter; directing the beam path of emitted radiation within a ring reflector through a gas sample; reflecting the beam path of emitted radiation around the ring reflector toward a detector, wherein the ring reflector comprises at least a portion of a spheroid shape; receiving the beam path of emitted radiation by the detector; and determining the at least one gas concentration of the gas sample based on the received beam path of emitted radiation.

A sixteenth embodiment can include the method of the fifteenth embodiment, further comprising filtering the beam path via a filter located between the emitter and the detector.

A seventeenth embodiment can include the method of the fifteenth or sixteenth embodiments, further comprising receiving two focused spots from the beam path by the detector, wherein the two focused spots are generated by astigmatism aberration within the ring reflector.

An eighteenth embodiment can include the method of any of the fifteenth to seventeenth embodiments, wherein a first focused spot is used to determine a sample signal and wherein a second focused spot is used to determine a reference signal.

In a nineteenth embodiment, a gas detector system may comprise at least one emitter configured to emit radiation in a beam path; at least one detector configured to receive at least a portion of the emitted radiation, wherein the emitted radiation generates at least two focused spots at the at least one detector; a ring reflector configured to direct the emitted radiation around the ring reflector toward the at least one detector, wherein the ring reflector comprises at least a portion of a spheroid shape, and wherein the ring reflector is configured to allow gas to flow through at least a portion of the beam path; and a processing circuit coupled to the one or more detectors configured to processes an output from the one or more detectors.

A twentieth embodiment can include the gas detector system of the nineteenth embodiment, wherein the pathlength of the beam path is at least approximately 20 millimeters.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A gas detector system comprising:
   at least one emitter configured to emit radiation in a beam path;
   at least one detector configured to receive at least a portion of the emitted radiation;
   a ring reflector configured to direct the emitted radiation around the ring reflector toward the at least one detector, wherein the ring reflector comprises at least a portion of a spheroid shape, and wherein the ring reflector is configured to allow gas to flow through at least a portion of the beam path;
   one or more reflectors configured to direct the beam path toward the at least one detector; and
   a processing circuit coupled to the one or more detectors configured to process an output from the one or more detectors.

2. The gas detector system of claim 1, further comprising one or more reflectors configured to direct the beam path from the emitter toward a wall of the ring reflector.

3. The gas detector system of claim 1, wherein the one or ore reflectors comprises a right angle prism.

4. The gas detector system of claim 1, wherein the one or more reflectors comprises two parallel mirrors.

5. The gas detector system of claim 1, wherein the emitted radiation generates at least two focused spots at the at least one detector.

6. The gas detector system of claim 5, wherein a first focused spot is used for a sample signal and a second focused spot is used for a reference signal.

7. The gas detector system of claim 1, wherein the emitter and the detector are oriented side by side in the same plane.

8. The gas detector system of claim 1, wherein the emitter and the detector are oriented opposite one another within the ring reflector in different planes.

9. The gas detector system of claim 1, further comprising at least one filter located such that the emitted radiation passes through the filter before reaching the detector.

10. The gas detector system of claim 1, further comprising:
    a second emitter configured to emit radiation in a second beam path; and
    a second detector configured to receive at least a portion of the emitted radiation in the second beam path, wherein the second beam path is oriented at an angle to the first beam path.

11. The gas detector system of claim 1, further comprising a plug configured to minimize gas flow through dead space within the ring reflector.

12. The gas detector system of claim 1, wherein the ring reflector comprises a diameter of between approximately 10 and 20 millimeters.

13. The gas detector system of claim 1, wherein the ring reflector comprises a width of between approximately 5 and 10 millimeters.

14. A method for gas detection comprising:
    generating a beam path of emitted radiation by an emitter;
    directing the beam path of emitted radiation within a ring reflector through a gas sample;
    reflecting the beam path of emitted radiation around the ring reflector, wherein the ring reflector comprises at least a portion of a spheroid shape;
    directing the beam path to a detector via one or more reflectors;
    receiving the beam path of emitted radiation by the detector; and
    determining the at least one gas concentration of the gas sample based on the received beam path of emitted radiation.

15. The method of claim 14, further comprising filtering the beam path via a filter located between the emitter and the detector.

16. The method of claim 14, further comprising receiving two focused spots from the beam path by the detector, wherein the two focused spots are generated by astigmatism aberration within the ring reflector.

17. The method of claim 14, wherein a first focused spot is used to determine a sample signal and wherein a second focused spot is used to determine a reference signal.

18. A gas detector system comprising:
    at least one emitter configured to emit radiation in a beam path;
    at least one detector configured to receive at least a portion of the emitted radiation, wherein the emitted radiation generates at least two focused spots at the at least one detector;
    a ring reflector configured to direct the emitted radiation around the ring reflector toward the at least one detector, wherein the ring reflector comprises at least a portion of a spheroid shape, and wherein the ring reflector is configured to allow gas to flow through at least a portion of the beam path;
    one or more reflectors configured to direct the beam path toward the at least one detector; and
    a processing circuit coupled to the one or more detector configured to process an output from the one or more detectors.

19. The gas detector system of claim 18, wherein the path-length of the beam path is at least approximately 20 millimeters.

\* \* \* \* \*